US010617885B2

(12) United States Patent
Flynn et al.

(10) Patent No.: US 10,617,885 B2
(45) Date of Patent: Apr. 14, 2020

(54) SYSTEM AND METHOD FOR AN INTENSITY MODULATED RADIATION THERAPY DEVICE

(71) Applicant: UNIVERSITY OF IOWA RESEARCH FOUNDATION, Iowa City, IA (US)

(72) Inventors: Ryan Flynn, Iowa City, IA (US); Junyi Xia, Iowa City, IA (US); Timothy J. Waldron, Iowa City, IA (US); Yusung Kim, Iowa City, IA (US); Bryan G. Allen, Iowa City, IA (US); Brennen N. Wears, Marshalltown, IA (US); Hongtao Ding, Coralville, IA (US)

(73) Assignee: University of Iowa Research Foundation, Iowa City, IA (US)

(*) Notice: Subject to any disclaimer, the term of this patent is extended or adjusted under 35 U.S.C. 154(b) by 481 days.

(21) Appl. No.: 15/408,824

(22) Filed: Jan. 18, 2017

(65) Prior Publication Data
US 2018/0200540 A1 Jul. 19, 2018

(51) Int. Cl.
A61N 5/00 (2006.01)
A61N 5/10 (2006.01)
(52) U.S. Cl.
CPC ......... A61N 5/1001 (2013.01); A61N 5/1045 (2013.01); A61N 5/1083 (2013.01)
(58) Field of Classification Search
CPC .................................................. A61N 5/1045
See application file for complete search history.

(56) References Cited

U.S. PATENT DOCUMENTS

| 4,450,578 A * | 5/1984 | Hill ........................... G21F 5/04 378/150 |
| 4,868,843 A | 9/1989 | Nunan |
| 6,240,161 B1 | 5/2001 | Siochi |
| 6,266,393 B1 | 7/2001 | Ein-Gal |
| 6,487,273 B1 | 11/2002 | Takenaka |
| 6,730,924 B1 | 5/2004 | Pastyr |
| 2005/0063516 A1 | 3/2005 | Kato |
| 2009/0001295 A1 | 1/2009 | Johnsen |
| 2012/0203490 A1 * | 8/2012 | Sayeh ....................... G21K 1/04 702/105 |

* cited by examiner

Primary Examiner — Dani Fox
(74) Attorney, Agent, or Firm — Smith Gambrell & Russell LLP

(57) ABSTRACT

Systems and methods for low energy radiation x-ray radiation therapy system for use at a target within a cavity of a subject. In an aspect, the system uses an aperture shaping device used to shape the radiation beam from the low energy radiation source. In an aspect, the aperture shaping device includes a plurality of leaf assemblies which include leaves configured to form the aperture and engage the radiation beam. In an aspect, the present invention utilizes a geared mechanics approach to create an aperture using only one dial input. The design ensures that the field size of the collimator remains a constant shape as it is opened and closed. In an aspect, the overall size of the collimator may be scaled to accommodate various radiation therapy requirements.

17 Claims, 10 Drawing Sheets

SYSTEM AND METHOD FOR AN INTENSITY MODULATED RADIATION THERAPY DEVICE

CROSS-REFERENCE TO RELATED APPLICATIONS

This application claims priority from PCT Application No. PCT/US2015/041070, filed Jul. 20, 2015, which claims priority to U.S. Provisional Patent Application No. 62/026,077, filed Jul. 18, 2014, and U.S. Provisional Patent Application No. 62/308,358, filed Mar. 15, 2016, the contents of which are incorporated herein by reference in their entirety.

BACKGROUND OF THE INVENTION

Technical Field

The invention applies to the fields of radiation therapy, and more particularly to a dynamic collimation system intended for use in intraoperative radiation therapy (IORT).

Related Art

Intraoperative radiation therapy (IORT) has advantages over conventional external beam radiation therapy (EBRT). For example, the biological effectiveness of a single, high dose of radiation is greater than the same dose administered in a fractionated (multi-session) regimen. IORT is performed in a single fraction, so IORT has been known as higher biological effectiveness when compared to small fractions of EBRT. Very high doses of 10-20 Gy can be delivered with IORT in a single treatment session since, unlike with conventional EBRT, the healthy tissues can be physically moved out of the radiation beam. When using IORT, the radiation is directed exactly on the area that a physician/surgeon intends to deliver radiation. Last, but not least, another advantage is the irradiation of the dose-limiting organ-at-risk (OAR) which is closely adjacent to tumor can be spared from radiation during surgery through the manual mobilization of healthy tissues from the treatment volume.

For this purpose, conventional IORT uses appropriate lead beam absorbers or through the proper use of an electron beam with energies that limit the depth of radiation penetration on deep structures. The current use of low energy x-ray for IORT applications is limited to mainly post-lumpectomy breast cancer radiation therapy in which the INTRABEAM® device (Carl Zeiss Meditec, Oberkochen, Germany) and accelerated partial breast irradiation using single- or multi-lumen high dose rate (HDR) applicators have been used. The single- or multi-lumen devices include Axxent® electronic brachytherapy system (iCAD, Inc., San Jose, Calif.), Contura® (Bard Biopsy Systems, Tempe, Ariz.) and MammoSite® ML (Hologic, Inc., Bedford, Mass.). A hybrid type, combining interstitial and single-entry intracavitary such as SAVI® (Cianna Medical, Inc., Aliso Viejo, Calif.) and ClearPath® (North American Scientific, Inc., Chatsworth, Calif.), has been introduced as well. The INTRABEAM® device has been also used for post-operative irradiation of brain tumors and cerebral metastases. INTRABEAM® is used as an immediate treatment subsequent to a stereotactic biopsy. Extended study reports of INTRABEAM® in the treatment of brain and cerebral tumors for both children and adults are available. The INTRABEAM provides a point source of 50 kV energy x-rays at the center of a spherical applicator. However, the use of the INTRABEAM device is limited to be used in conventional IORT applications such as pancreatic cancer, retroperitoneal sarcoma, and selected genitourinary malignancies, since it is designed specifically for intracavitary application.

The current standard technique of modern IORT is to use electron energy of 3-12 MeV. This electron based IORT technique utilizes an applicator, which is a set of acrylic cylinders with different sizes, to shape radiation beams. The electron based IORT is performed in the shielded operation rooms in which a miniaturized and mobile-linear accelerator (Mobetron, Intraop Medical, Inc., Sunnyvale, Calif., USA) have been installed. However, the Mobetron system is large ($4.91$ m$^3$=1.98 m×1.03 m×2.41 m) and heavy (2937 lbs) so it is difficult for clinicians to transfer the system among different operation rooms. Also, due to its high energy (6, 9, 12 MeV), the Mobetron system cannot be used in a regular operation room without sufficient shielding.

In addition, traditional IORT systems are either very large, such as the Mobetron system, or require several feet of shielding, such as an operating room that is inside a vault housing a linear accelerator. There is also a problem in defining specific radiation doses as a function of position in the region to be treated. Further, IORT systems traditionally require number therapy sessions. Lastly, traditional IORT systems, and their radiation sources, are limited in orientation options in regards to the subject. For example, many cannot be placed inside or above the surgical cavity of a patient.

Therefore, there is a need for a system and method that overcomes the limitations discussed above while meeting the aforementioned goals.

SUMMARY OF THE INVENTION

In an aspect, the invention is a system and method for compact intraoperative low-energy radiation therapy. In an aspect, the system and method require no additional room shielding in operating rooms in which it is intended for use. In an aspect, the invention has a very small footprint and does not require any shielding. The invention overcomes a major problem associated with intraoperative radiation therapy (IORT), which is that defining specific radiation doses as a function of position in the region to be treated is a non-trivial process.

In an aspect, the system is configured to allow a user to define arbitrary radiation doses both on the surface and at depth inside the cavity of the subject to be treated. In an aspect, the system includes a compact collimation system. In an aspect, the system is configured to utilize a compact collimation system of low-energy x-ray. Such a system enables clinicians to overcome these limitations of current low-energy x-ray solution (INTRABEAM®) for IORT. The system has the ability to deliver highly conformal radiation dose distributions in the surgical suite following tumor resection that improves tumor control rates. This improves outcomes and enables a reduction in the number of external beam radiation therapy sessions that the patient must undergo following surgery, reducing cost and improving convenience for patients. Further, in an aspect, the size of the compact collimation system is configured to be a fraction of the size of traditional systems, including the Mobetron system. In an aspect, the present invention includes a collimator used to dynamically shape radiation beams in IORT in head and neck cancer, sarcoma, lung cancer and related treatments. In an aspect, the collimator is compact and used close to a treatment site inside a surgical cavity to increase the radiation dose rate and reduce the treatment time. In an aspect, the overall size of the collimator is scaled to accommodate various radiation therapy requirements.

In an aspect, the collimation system can be utilized in dynamic delivery of the radiation dose. In such aspects, the collimation system can include a robotic arm on which the collimator is coupled. The robotic arm can move the collimator above the surgical cavity while delivering the radiation. Multi-leaf collimation is used to provide conformal shaping of the radiotherapy treatment beams. In an aspect, the present invention utilizes a geared mechanics approach to create an adjustable aperture from multiple leaves within the compact collimator. In an aspect, the collimator can create a rectangular aperture from four leaves. In this exemplary aspect, the design ensures that the field size of the aperture of the compact collimator remains a constant shape as it is opened and closed. In an aspect, the size of the adjustable aperture can change during the treatment plan, changing size between locations.

In an aspect, the collimator can create the aperture using only one dial input to move the multiple leaves. In an exemplary aspect, the one dial input can be configured to move four (4) leaves. In an aspect, the leaf positions of the four leaves can be controlled with two separate drive motors, one motor for each orthogonal direction. In another aspect, three motors can be used to move four leaves; one motor to control one parallel leaf pair, and the other two to control the remaining two leaves independently. In another aspect, four motors can be used to control all four leaves independently. In another aspect, one or more motors can be used for added redundancy by taking control of the leaves that are associated with one or more motors that may fail during radiation delivery. In other aspects, the number of leaves and motors can vary depending on the desired shape of the aperture of the collimator.

These and other objects and advantages of the invention will become apparent from the following detailed description of the preferred embodiment of the invention. Both the foregoing general description and the following detailed description are exemplary and explanatory only and are intended to provide further explanation of the invention as claimed.

The accompanying drawings are included to provide a further understanding of the invention and are incorporated in and constitute part of this specification, illustrate several embodiments of the invention, and together with the description serve to explain the principles of the invention.

DETAILED DESCRIPTION OF THE INVENTION

Figure 1:
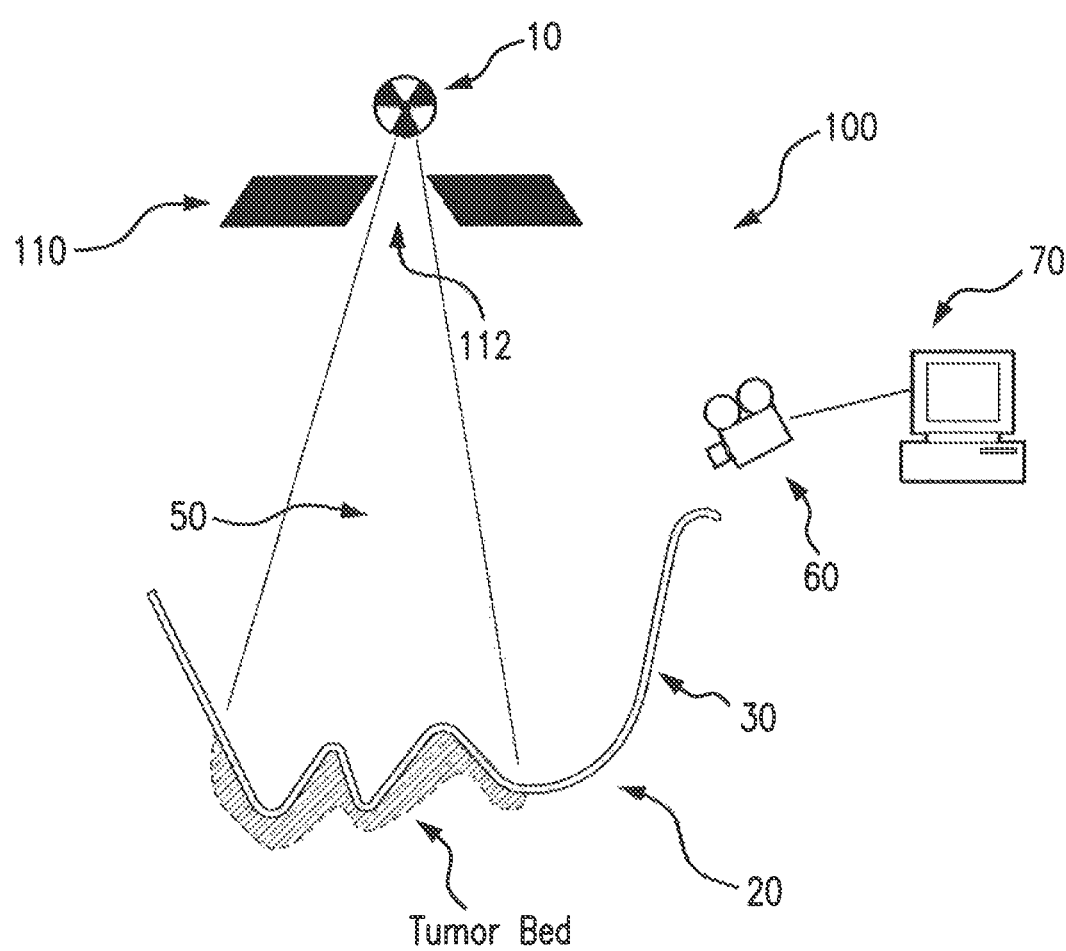
FIG. 1 illustrates an intraoperative x-ray therapy system according to an aspect of the present invention.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, aspects of the current invention may take the form of an entirely hardware embodiment, an entirely software embodiment, or an embodiment combining software and hardware aspects. In an aspect, the current invention can include a combination of physical components configured to perform certain steps and functions (e.g., generating ion beams, moving trimmers configured to shape ion beams, etc.) that are controlled by a combination of hardware and software components. Furthermore, components of the methods and systems may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Further, components and methods utilized by the present invention as described below can be performed in a program environment, which may incorporate a general-purpose computer or a special purpose device, such as a hardware appliance, controller, or hand-held computer. In addition, the techniques of the components described herein can be implemented using a variety of technologies known in the art. For example, the methods may be implemented in software executing on a computer system, or implemented in hardware utilizing either a combination of microprocessors or other specially designed application specific integrated circuits, programmable logic devices, or various combinations thereof.

Some aspects of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer readable memory that can direct a computer or other programmable data processing apparatus to function in a particular manner, such that the instructions stored in the computer-readable memory produce an article of manufacture including computer readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The invention is directed to an intraoperative radiation therapy (IORT) system. More specifically, the invention is directed to a system and method of low-energy X-ray radiation therapy (herein LexRT). The LexRT system 100, as illustrated in FIG. 1, can be used to overcome limitations of conventional IORT systems to deliver intensity-modulated radiation therapy.

In an aspect, the LexRT system 100 is configured to use a low-energy x-ray source 10 for the treatment of various forms of cancer treated with radiation therapy in a surgical setting. The types of cancer can include, but are not limited to, sarcomas, lung cancer, pancreatic cancer, and any target 20 found within a cavity 30 of the subject being treated. The LexRT system 100 can deliver intensity-modulated radiation therapy to the targets 20, in which the intensity modulation is achieved using an aperture shaping device 110 to control the strength and shape of the field of radiation/radiation beam 50 generated by the radiation source 10. In an aspect, the aperture shaping device 110 can comprise an x-ray collimation system 110. In an exemplary aspect, the x-ray collimation system 110 can comprise a multi-leaf collimator (MLC) 110 specifically designed for shaping a radiation beam 50, through an adjustable aperture 112, generated by an x-ray source 10, discussed in more detail below. As illustrated in FIG. 1, the LexRT system 100 can further comprise a surface monitoring system 60, and a computer/computing means 70.

In an aspect, the x-ray source 10 is a low energy x-ray source 10. Such low energy x-ray sources can include, but is not limited to, a kilovoltage-range x-ray source 10. In an exemplary aspect, the low energy x-ray source 10 can range between 50 KV to 69 KV. However, other low energy sources 10 can be used with the LexRT system 100.

Figure 4:
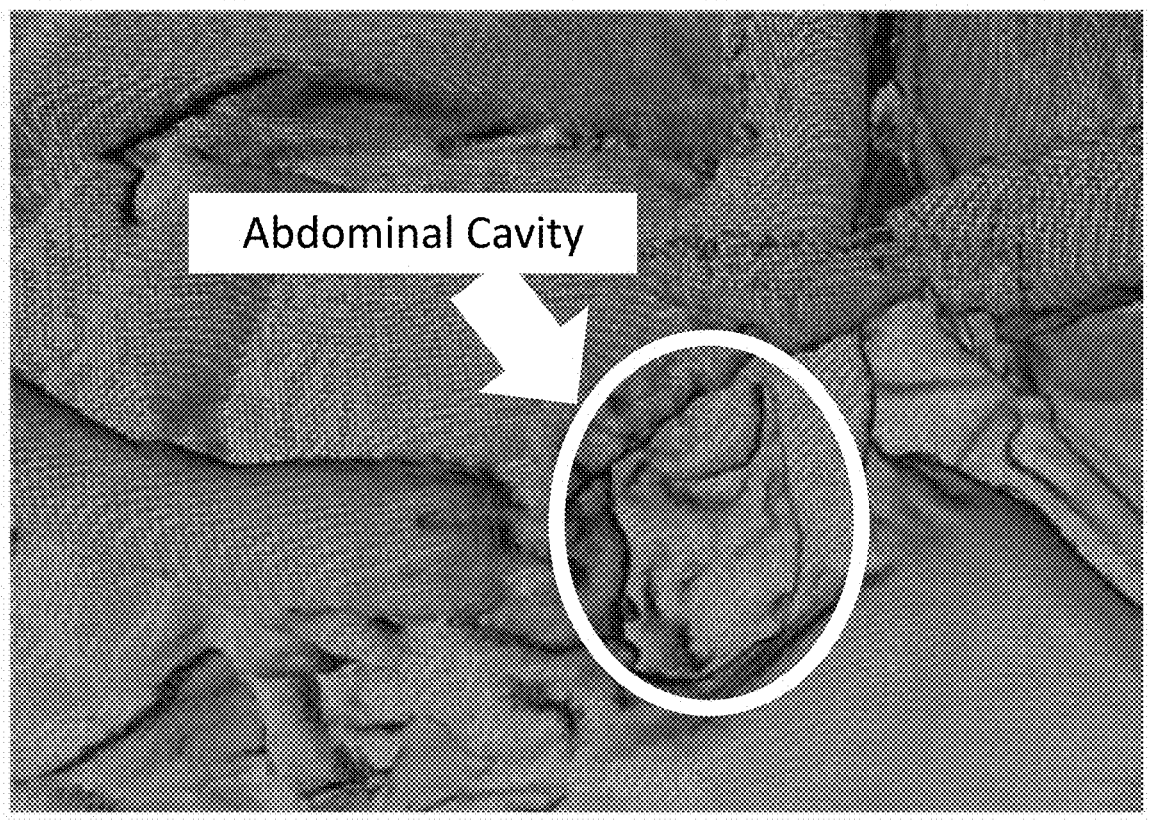
FIG. 4 illustrates a 3D surface reconstruction created by a real-time 3D surface imaging system according to an aspect of the present invention.

In an aspect, the LexRT system 100 can be configured to digitize the treated surface 20 and surrounding tissue in a computer model by capturing a surface image using a surface monitoring system 60. In an aspect, the surface monitoring system 100 can be a 3D surface monitoring system 60. In an aspect, the 3D surface monitoring system 60 can include a real-time 3D surface imaging system 60. In an aspect, the real-time 3D surface imaging system 60 includes 3D depth cameras, a processor, and signal processing software. Examples of surface monitoring devices include, but are not limited to, the Kinect system (Microsoft Corporation, Redmond, Calif.), the AlignRT system (Vision RT Ltd, London, UK), the CRad Catalyst system (C-RAD AB, Sweden), or any other device configured to capture an image digitally for use with a computer model. FIG. 4 illustrates a 3D abdominal cavity generated by the real-time 3D imaging system 60. In other aspects the imaging system can be configured to have accuracy to 2 mm through use of a higher resolution 3D camera system and improved reconstruction algorithms, which is sufficient for accurate radiation dose calculation.

After capturing a digital image of the surface of the target 20 and surrounding tissue, a radiation plan in which the tissues/target 20 to be treated and the doses desired are rapidly defined by computerized means 70, discussed below. The surface imaging system 60 can also be controlled and work with the computer 70. Following the generation of the radiation plan, the dose is delivered to the patient.

In an aspect, the combination of the surface imaging system 60 and computerized means 70 used in the generation of the radiation plan by the LexRT system 100 is used to rapidly acquire the tissue map at a variable temporal rate following the initial surface capture of the target 20 and during the radiation process. Each acquired tissue map will be registered to a reference map to quantify the tissue motion that occurred during the delivery. Motion thresholds can be defined on a point-by-point basis, if the tissue motion exceeds the motion threshold, the radiation beam 50 will be paused while the clinical team intervenes. Intervention can be by moving the tissue back to the original configuration, applying suction to remove fluid buildup, or by generating a new, adapted, radiation plan based on the new tissue configuration. Once the intervention is complete, the beam 50 is turned back on and the treatment proceeds.

In an aspect, the aperture shaping device 110 can be configured for use with a low-energy x-ray source 10 and the surface imaging system 60 and computerized means 70 to treat a target 20 of the subject. In addition, the aperture shaping device 110 can be compact, discussed in more detail below. In an aspect, the LexRT system 100 can be configured to deliver the desired dose distribution/shaped-beam 50 to the target 20 within the surgical cavity 30 by intensity modulation through the use of an aperture shaping device 110 configured to interact within the radiation beam 50 by temporal and spatial modulation. The surface monitoring system 60 provides images for treatment planning and motion monitoring of surgical cavity 30. In an exemplary aspect, the aperture shaping device 110 is configured to weigh about 100 lbs., which is about 3% of the weight of the Mobetron system discussed above.

In an aspect, the LexRT system 100 can be configured to deliver intensity modulated radiation therapy by means of temporal modulation by physically moving the field of the energy beam 50, defined by an aperture 112 within the aperture shaping device 110, to a range of positions throughout the treatment region. At each position, the intensity of radiation delivered to the tissue/target 20 can be defined by controlling the amount of time the source 10 points at the position or by changing the distance between the source 10 and the tissue 20.

Figure 2A:
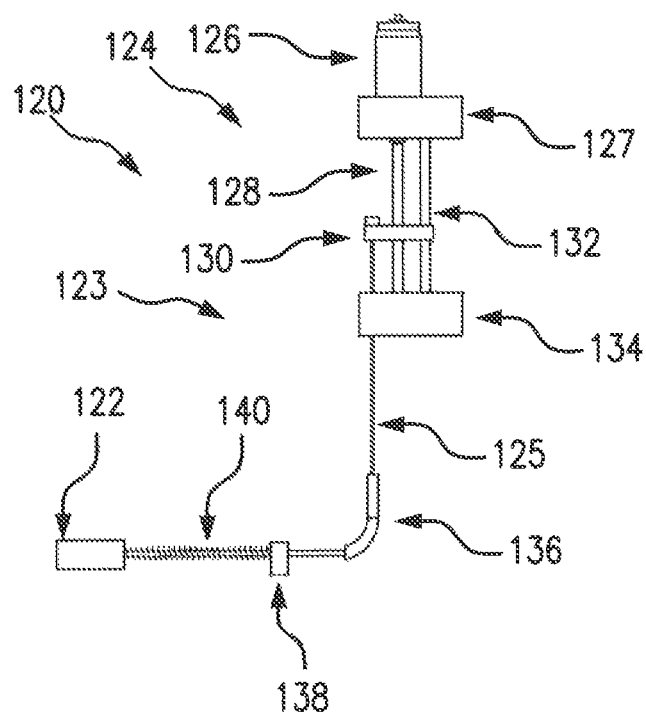
FIG. 2a is a schematic representation of a single leaf assembly of an x-ray collimation system according to aspects of the present invention.
Figure 2B:
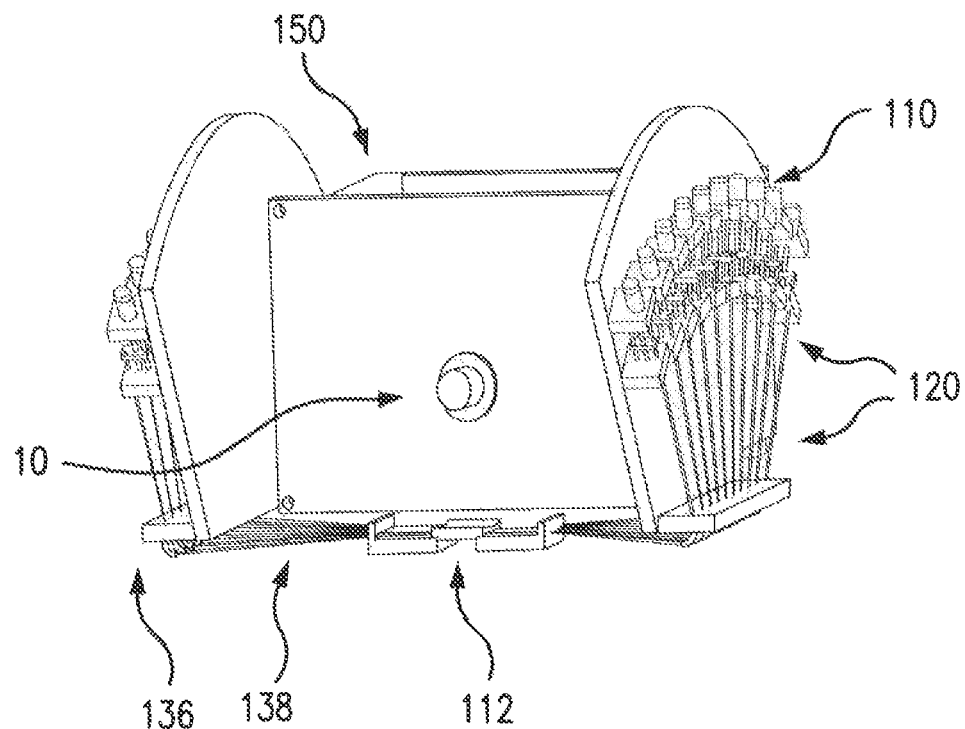
FIG. 2b is a schematic representation of an of an x-ray collimation system according to aspects of the present invention.

FIGS. 2a-b illustrate an aperture shaping device 110 in the form of a collimation system 110 according to an aspect of the present invention. More specifically, FIGS. 2a-b illustrate an x-ray collimation system 110 in the form of a multi-leaf collimator 110. In an aspect, the collimation system 110 comprises a series of leaf assemblies 120 mounted on a housing 150. The housing 150 can house the x-ray source 10. The leaf assemblies 120 include a leaf 122, a motion translation assembly 123, and a driving mechanism 124. The series of leaf assemblies 120 can be configured to operate independently from one another in order to position their individual leaves 122 to shape the x-ray beam 50 as it exits an aperture 112 of the housing 150. The leaves 122 can be comprised of various radiation blocking materials known in the art. In addition, the leaves 122 can take various shapes and forms, including, but not limited to, rectangular.

FIG. 2a illustrates a configuration of a single leaf assembly 120 of the x-ray collimation system 110 of FIG. 2b. Each leaf 122 is connected to a motion translation assembly 123 that is driven by a driving mechanism 124. As illustrated, the motion translation assembly 123 is configured to translate a linear motion from the driving mechanism 124 in one direction to another direction of linear motion to control the movement of the leaf 122. In an aspect, the motion translation assembly 123 translates the linear motion from the driving mechanism 124 approximately ninety (90) degrees.

In an aspect, the driving mechanism 124 comprises a stepper motor 126 configured to drive a lead screw 128, nut 130, and guide 132 combination. The motion translation assembly 123, components of which are discussed below, is then actuated by the stepper motor 126 to move the leaf 122. The computerized means 70 can be configured to control the activity of the driving mechanism 124. The stepper motor 126 can be coupled to a motor mount 127 attached to the housing 150 of the x-ray collimation system 110.

The motion translation assembly 123, as illustrated in FIG. 2a, includes a connecting wire 125 and guide mount 134, discussed in more detail below. The connecting wire 125 is connected to the leaf 122. The lead screw 128 attached to the stepper motor 126 is used to translate the motor's radial motion into a linear motion to control the movement of the connecting wire 125. The nut 130 connected to the connecting wire 125, wherein the nut 130 is driven along the lead screw 128, controls the movement of the connecting wire 125. A guide 132 can be used with the nut 130 to translate the linear motion to the connecting wire 125. A guide mount 134, connected to the housing 150, can be used to assist with the guide 130. The guide 130 can be anchored between the guide mount 134 and motor mount 127 for each leaf assembly 120. In addition, the guide mount 134 can include an aperture (not shown) through which the connecting wire 125 can travel linearly.

In an aspect, the connecting wire 125 is configured to be bendable. In such aspects, the bendable connecting wire 125 can translate the linear motion of the motor 126, more specifically the nut 130 driven by the lead screw 128, allowing for the motor 126 to be placed at different angles and distances from each leaf 122. This allows the motors 126 to be placed above the leaves 122, creating a more compact configuration of the leaf assemblies 120 within the housing 150 of the collimator 110. A wire mount 136, shown along the bottom of the housing 150, can assist with the bending of the connecting wire 125. In an aspect, the wire mount 136 can include a wire guide aperture (not shown) that assists with the guiding of the connecting wire 125.

The leaf 122 can be found on the end of the connecting wire 125 opposite the driving mechanism 124. The leaf 122 can be supported by a leaf mount 138. A compression spring 140 can be placed between the leaf mount 138 and the leaf 122. The compression spring 140 is configured to keep the connecting wire 125 in tension and act as a failsafe by closing the leaf 122 if a component in the x-ray collimation system 110 were to break or fail. Wire tension also helps to improve the position accuracy of the leaf 122. The leaves 122 of the leaf assemblies 120 can be arranged so as to function to shape the aperture 112 through which the radiation beam 50 travels. As shown in FIG. 2b, the leaves 122 are arranged in two parallel rows opposite each other to form the aperture 112. However, in other embodiments, the leaves 122 can have other desired arrangements, including, but not limited to, circular placement.

Figure 3A:
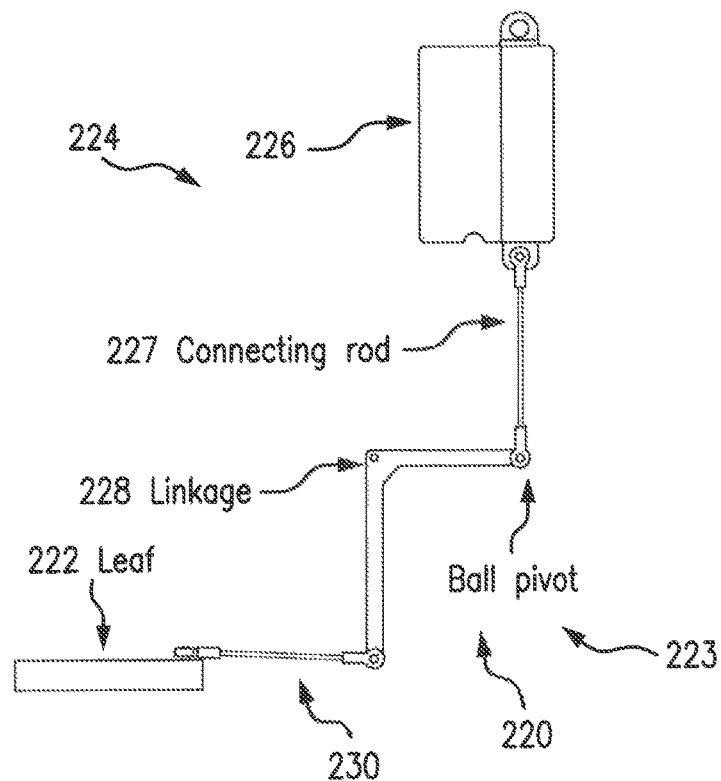
FIG. 3a is a schematic representation of a single leaf assembly of an x-ray collimation system according to aspects of the present invention.
Figure 3B:
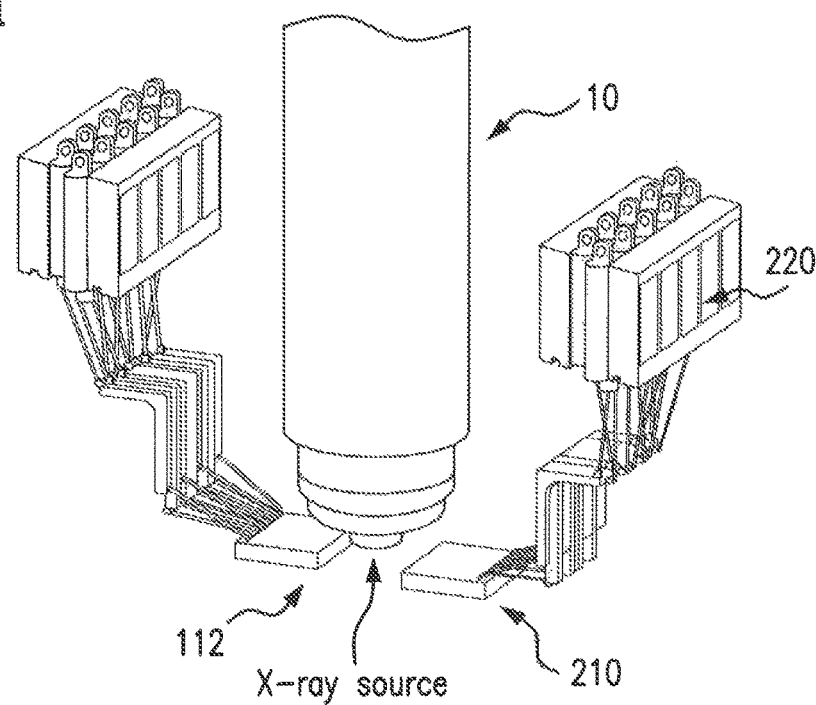
FIG. 3b is a schematic representation of an x-ray collimation system according to aspects of the present invention.

FIGS. 3a-b illustrate leaf assemblies 220 of an x-ray collimation system 210 according to another embodiment of the present invention. The collimation system 210 as illustrated in FIGS. 3a-b can include a housing (not shown), and housing components, similar to the collimation system 110 illustrated in FIG. 2b. The leaf assemblies 220 of the current embodiment provide the same function as those described in relation to FIGS. 2a-b, including leaves 222, a motion translation assembly 223, and a driving mechanism 224. Namely, the individual leaf assemblies 220 include a leaf 222 that is driven/controlled by a driving mechanism 224.

In an aspect, the driving mechanism 224 comprises a linear actuator 226 with a connecting rod 227. The linear actuator 226 can be controlled by the computing means 70 discussed above and below. The linear actuator 226 drives the motion translation assembly 223 to drive the leaf 222. The motion translation assembly 223 comprises a linkage 228 and a leaf connecting rod 230. The connecting rod 227 is connected to the linkage 228. The linkage 228 is then connected to the leaf 222 through a leaf connecting rod 230. In an aspect, the connecting rod 227 is pivotably connected to both the linear actuator 225 and the linkage 228 and the linkage 228 is pivotably connected to the leaf connecting rod 230. In addition, the linkage 228 can be pivotably connected to the housing or other linkages 228 of other assemblies 220 at a midpoint. In an aspect, ball pivot joints are used to increase the degrees of freedom between the connecting rods 227, 230 and the linkage 228 to allow the driving mechanism 224, comprising the actuators 226 and connecting rods 227, to be positioned out of the line of motion of the leaves 222 while translating the vertical linear motion of the driving mechanism 224 into a horizontal linear direction of movement of the leaf 222. This allows the actuators 226 to be placed above the leaves 222 to reduce the size of the device 210. As shown in FIGS. 3a-b, the linkage 228 has an L-shape to assist in this translation.

Figure 5:
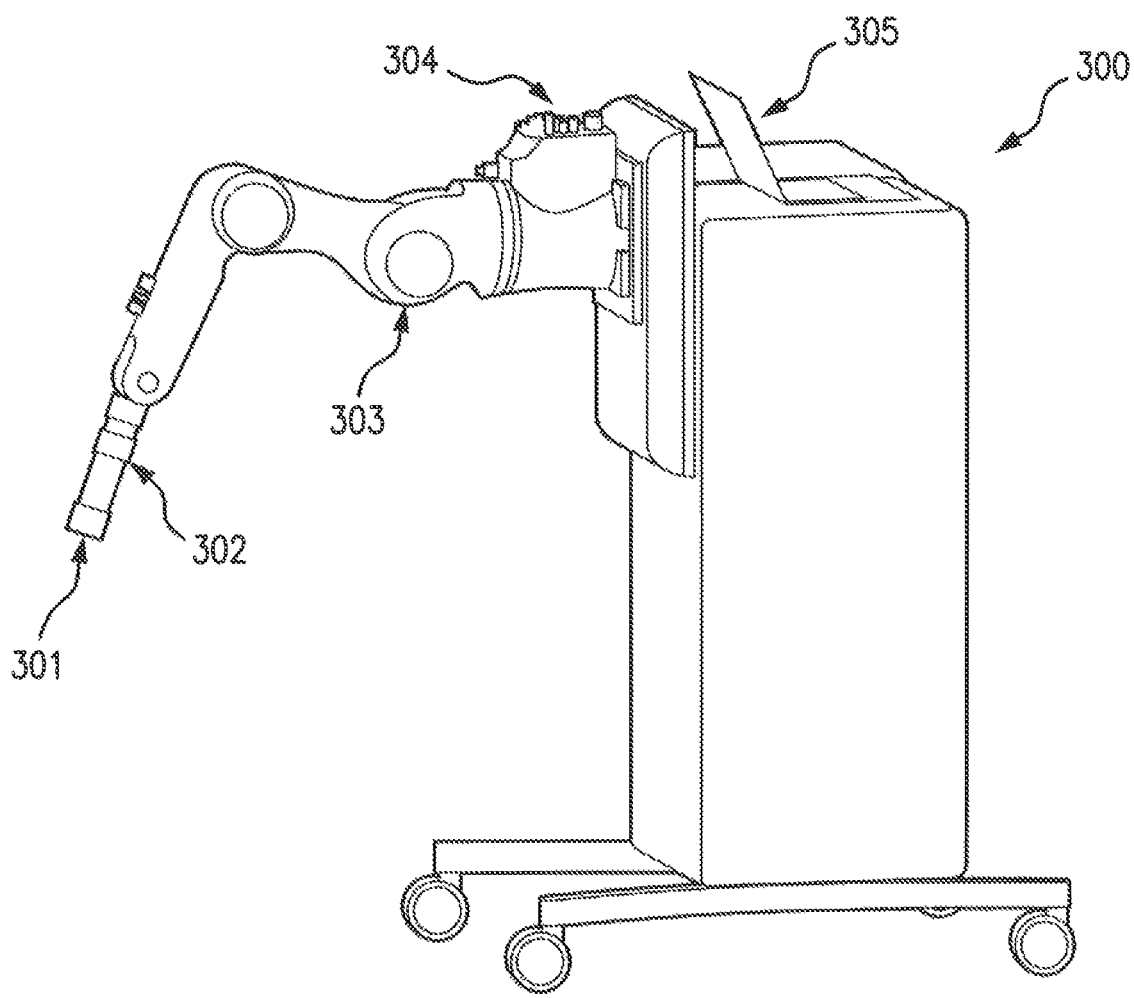
FIG. 5 provides a system overview of a low-energy radiation therapy device equipped with a compact collimation system according to an aspect of the present invention.
Figure 6A:
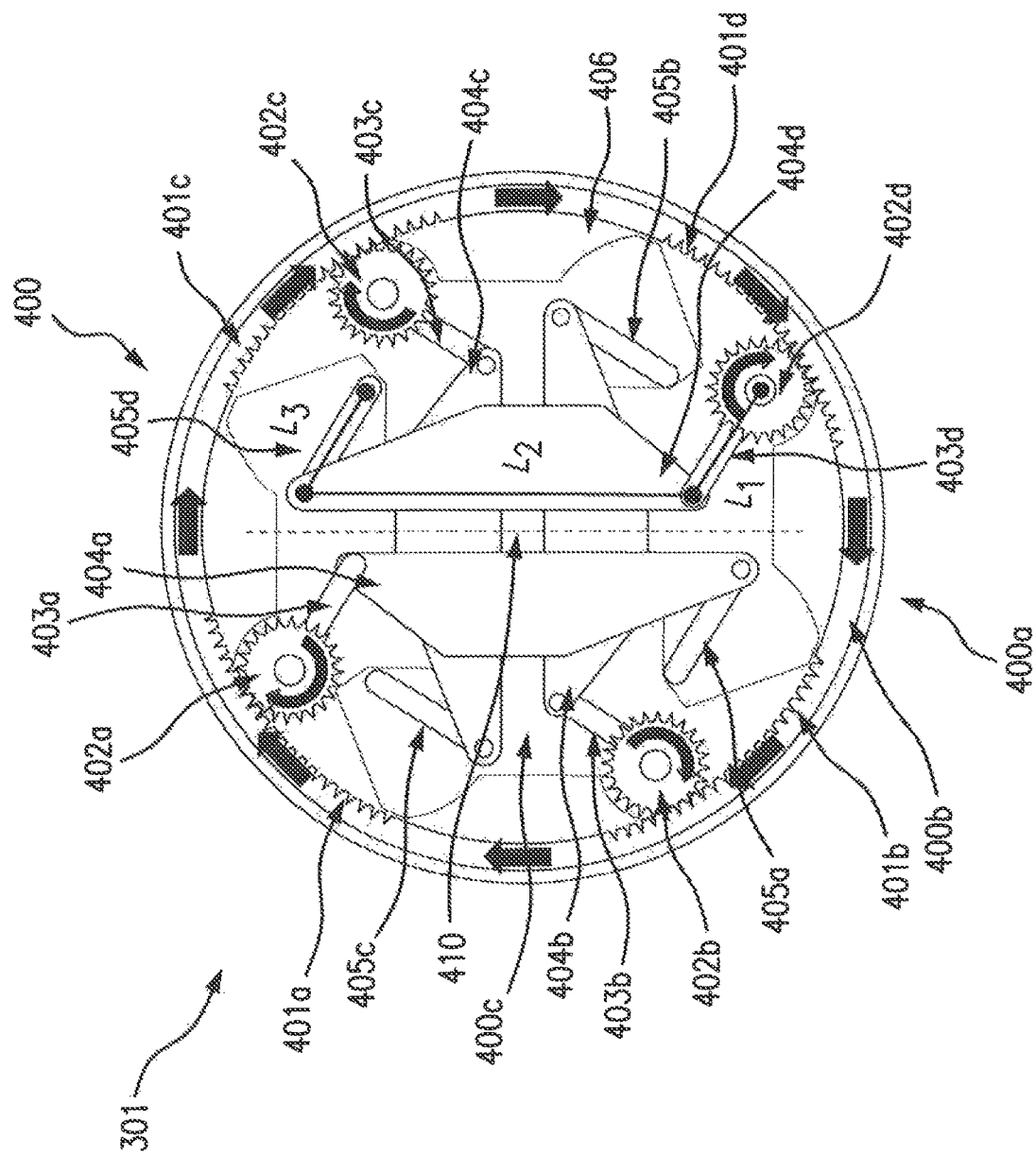
FIG. 6a is a schematic representation of components of a compact collimator according to aspects of the present invention.
Figure 6B:
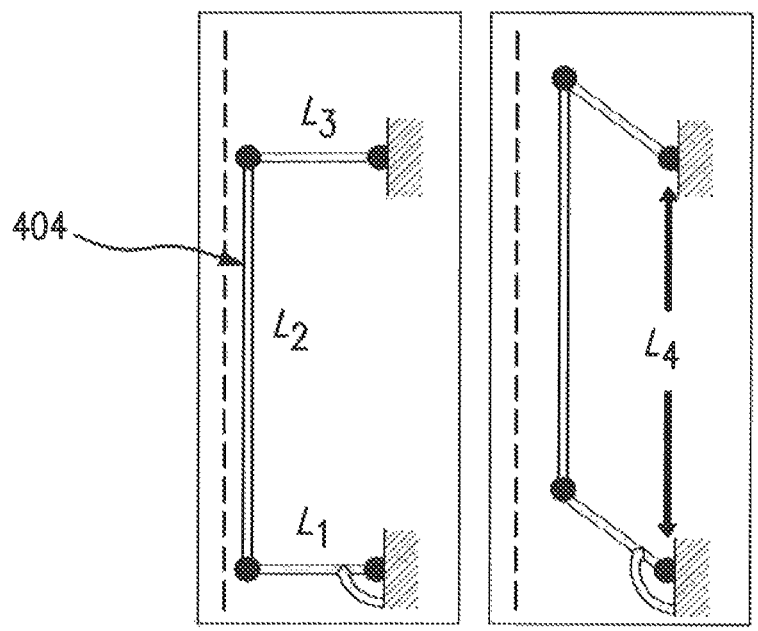
FIG. 6b is an applied kinematics diagram of the compact collimator of FIG. 6a according to aspects of the present invention.
Figure 6C:
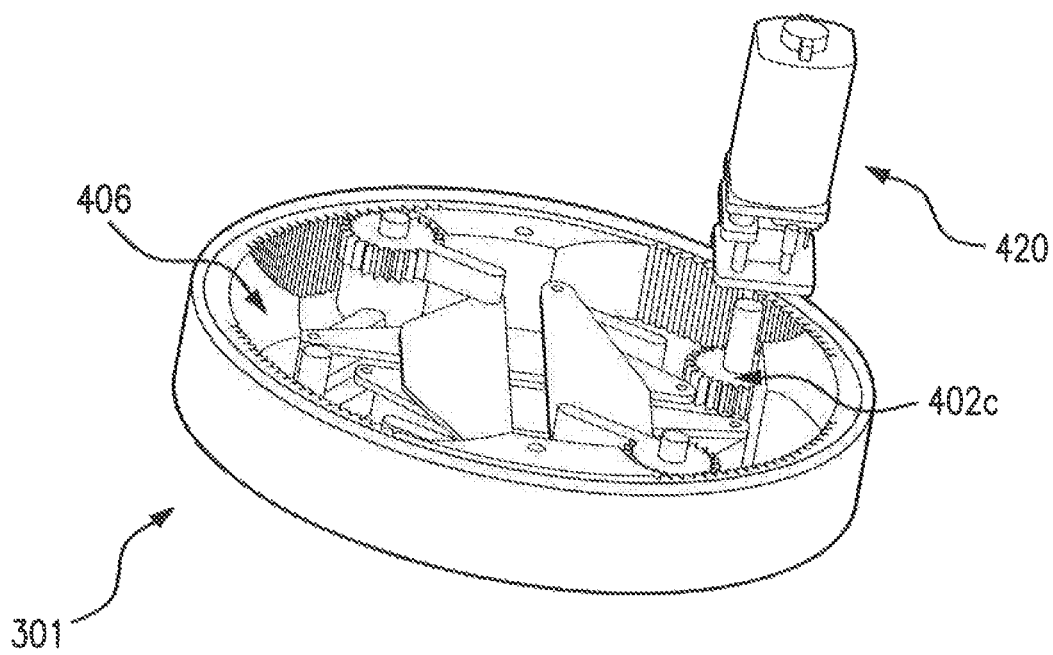
FIG. 6c illustrates the mechanics of a compact collimation system according to aspects of the present invention.
Figure 6D:
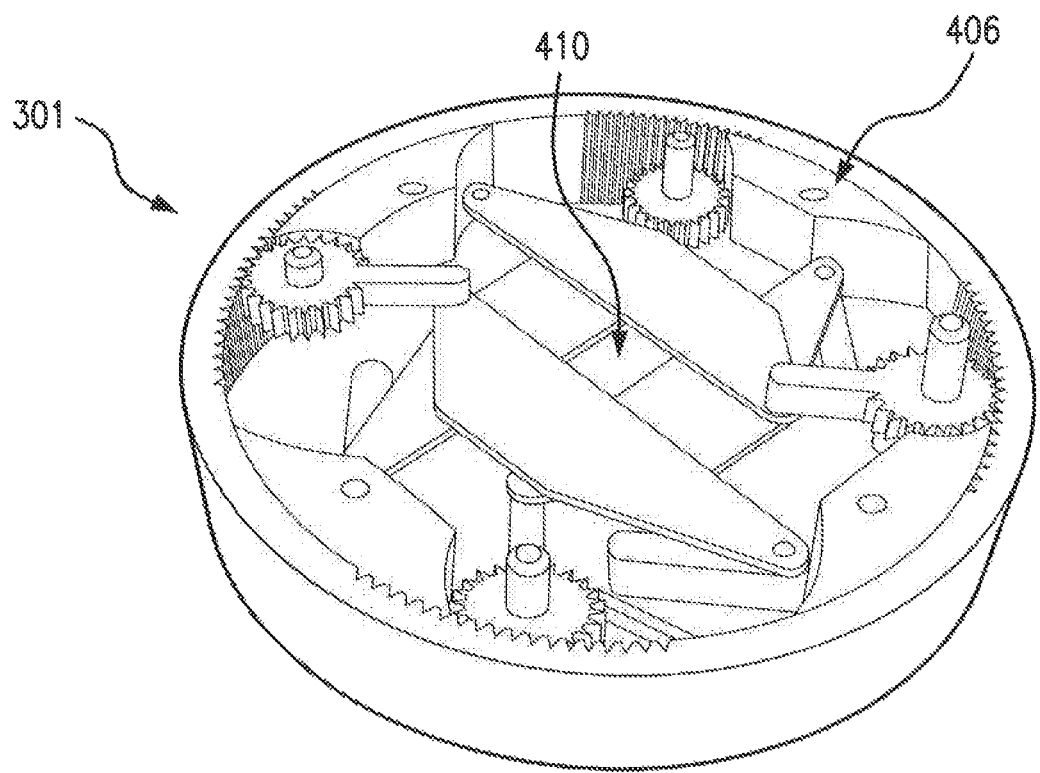
FIG. 6d illustrates portions of the internal hardware of a compact collimation system according to aspects of the present invention.
Figure 7:
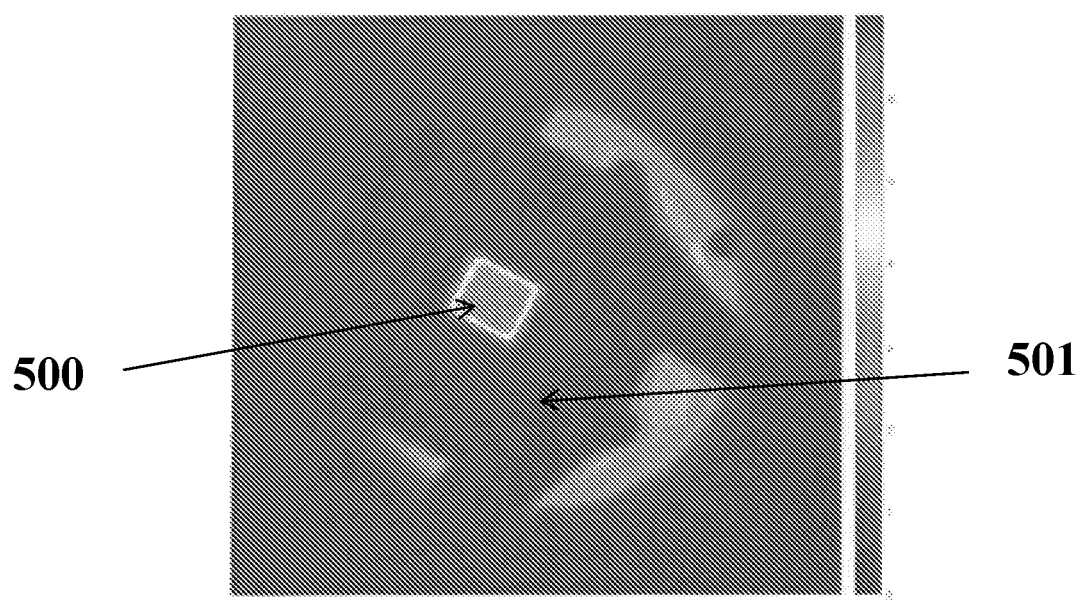
FIG. 7 illustrates a radiation dose measurement for a collimator according to an aspect of the present invention.

FIGS. 5-7 illustrate a compact collimation system 300 according to another aspect of the present invention. The compact collimation system 300 is configured for dynamically shaping the radiation beam for a low-energy therapy. In an aspect, the low-energy therapy can take the form of LexRT. FIG. 5 illustrates a LexRT system 300 equipped with a compact collimation system 301 according to aspects of the present invention. The compact collimation system 301 attaches to the proximal end of the housing of a radiation source 302 such that the beam of the radiation source passes through an aperture of the compact collimation system 301. In an aspect, the collimation system 301 can be fitted to the housing of radiation source 302 via fasteners known in the art. Such fasteners can include, but are not limited to, mechanical. magnetic, and other various fastener types. However, it is preferable that the fasteners be adjustable and reusable. In other aspects, a mounting bracket can be used to couple the collimation system 301 and the housing of the radiation source 302.

The compact collimation system 301 is used to control the strength and shape of the field of radiation/radiation beam generated by the radiation source 302. The radiation source 302 can be an x-ray radiation source that emits photons. In an aspect, a radiation source that emits photons in the kilovoltage energy range is preferred. In other aspects in which thicker collimator leaves are utilized, radiation sources within the megavoltage range can be utilized. In preferred aspects, the energy range corresponds to the thickness of the leaves In an aspect, the distal end of the radiation source 302 attaches to a robotic arm 303. Similar to the connection between the x-ray source 302 and the collimation system 301, the x-ray source 302 can be connected with fasteners to the robotic arm 303. Such fasteners can be mechanical, reusable, and adjustable. In a preferred embodiment, the robotic arm 303 includes a six degree of freedom range of motion. The robotic arm 303 can include those arms known in the art. For example, the robotic arms employed by the Accuracy CyberKnife and the Zeiss IntraBeam can be utilized by the present invention. The robotic arm 303 is used to maneuver the x-ray radiation source 302 such that radiation source 302 may be placed inside or above the surgical cavity of a patient.

In an aspect, the robotic arm 303 may be manually controlled from a control system 304. In another aspect, the robotic arm 303, the x-ray radiation source 302 and the compact collimation system 301 may be controlled through a treatment planning system run on a computer 305. In some aspects, a separate delivery computer (not shown) can be used to control the motion of the robotic arm 303. In such aspects, the delivery computer can take instructions from the treatment planning system (on computer 305) and/or the individual operating the control system 304. The treatment planning system, via the computer 305, can implement a radiation treatment plan and monitor the activities in a surgical cavity, including the motion of the compact collimator system 301. To deliver non-uniform doses that conform to irregular targets both laterally and in depth, the robotic arm 303 moves the compact collimation system 301 and the radiation source 302 along an optimal path, with the aperture (discussed below) being placed at each dwell position determined by either the user of the control system 304, the computer 305 running the treatment planning system, or the delivery computer.

FIG. 6a illustrates components of the compact collimation system according to aspects of the present invention. In an aspect, the compact collimation system 301 features a circular hardware housing 400. The hardware housing 400, and other materials of the compact collimation system 301, can be made from any material that can adequately block the radiation dose of the radiation source 302 while conforming to medical material standards. For example, such materials can include, but are not limited to, stainless steel and aluminum.

In an aspect, the dimensions of the housing 400 of the compact collimation system 301 correspond to the dimensions of the housing of the radiation source 302. In an exemplary aspect, the housing 400 is approximately 67.5 mm in diameter while the housing of the radiation source 302 is approximately 60 mm in diameter, allowing the housing 400 of the compact collimation system 301 to encompass the housing of the radiation source 302.

The housing 400 includes an exterior wall 400a that contains a rotating large internal gear 400b (see arrows). The exterior wall 400a is configured to retain the large internal gear 400b while allowing the larger internal gear 400b to rotate within the housing 400, with the exterior of the internal gear 400b slidably engaging the interior surface of the exterior wall 400a. In an aspect, the exterior wall 400a includes a base section 400c which supports components of the compact collimation system 301, including the internal gear 400b.

Embedded in the interior wall surface of the internal gear/housing 400b are teeth/cog regions 401a, 401b, 401c, 401d. The teeth/cog regions 401a, 401b, 401c, 401d interface with smaller gears 402a, 402b, 402c, 402d, discussed further below, respectively. In an aspect, the teeth/cog regions 401a, 401b, 401c, 401d are equally spaced from one another along the interior wall of the internal gear 400b. Flat surfaces can be found between the regions 401a, 401b, 401c, 401d of the internal gear 400b. The flat surfaces slidably engage protrusions 406, which, along with the exterior wall 400a and the base section 400c, keep the large internal gear 400b in place while allowing the large internal gear 400b to rotate within the housing 400 of the compact collimation system 301.

The smaller gears 402a, 402b, 402c, 402d may be constructed from plastic, metal, or any other suitable material and use stainless steel dowel pins (not shown) to attach to the base 400c of the housing 400. The mesh/interface of the equally spaced teeth/cog regions 401a, 401b, 401c, 401d and the smaller gears 402a, 402b, 402c, 402d enable the translation of rotational motion to the large internal gear 400b, with the protrusions 406 limiting the extent of the rotational motion of the large internal gear 400b and the smaller gears 402a, 402b, 402c, 402d.

Each small gear 402a, 402b, 402c, 402d uses an arm (403a, 403b, 403c, 403d) to individually connect to a leaf 404a, 404b, 404c, 404d. In an aspect, the leaves 404 are constructed from tungsten. However, the leaves 404 may be constructed from any material know in the art suitable for shielding radiation. In addition, the thickness of the leaves 404 can be determined based upon the strength of energy of the radiation source 302. In an aspect, the gear arms 403a, 403b, 403c, 403d are pivotally connected to the leaves 404a, 404b, 404c, 404d. Leaf arms 405a, 405b, 405c, 405d are connected to the end of leaves 404a, 404b, 404c, 404d opposite the gear arm 403a, 403b, 403c, 404d connection. The leaf arms 405a, 405b, 405c, 405d are pivotally connected to the leaves 404a, 404b, 404c, 404d at one end and are pivotally connected to base 400c of the housing 400 at the other end. All the pivoting connections of the gear arms 403, leaves 404, and leaf arms 405, including those with the base 400c, can utilize pins (not shown).

The collimation system 301 effectively shapes a photon beam from the radiation source 302 as it exits an aperture 410 formed by the interior sides of the leaves 404. As shown in FIG. 6b, the pivoting mounting of the leaves 404 restricts the movement of the leaves 404 in a perpendicular direction towards or away from the small gears 402 and the pivot mounts of the leaf arms 405 to the base 400c while the edges of the leaves 404 remain substantially parallel throughout the movement. For example, referring to FIG. 6a, leaves 404a and 404c are positioned parallel to each other and perpendicular to leaves 404b and 404d. Leaves 404b and 404d are positioned parallel to each other and perpendicular to leaves 404a and 404c. Due to the orthogonal orientation of the leaves 404a, 404b, 404c, 404d, the leaves 404a, 404b, 404c, 404d being pivotally mounted at one end to the gear arms 403a, 403b, 403c, 403d and pivotally mounted the leave arms 405a, 405b, 405c, 405d at the opposite end, rotational motion of gears 402a, 402b, 402c and 402d translates to linear motion of the leaves 404a, 404b, 404c, 404d along their length while allowing the edges of the leaves 404 adjacent the aperture 410 to increase or decrease the size of the aperture 410. The combination of the linear and perpendicular motions of leaves 404a, 404b, 404c and 404d causes a variable size rectangular shaped aperture 410 to be formed in the collimation system 301. The aperture 410 of the compact collimation system 301 is augmented according to the position of the leaves 404a, 404b, 404c, 404d.

The orientation of the leaves 404a, 404b, 404c, 404d and their number impact the shape and size of the aperture 410. As shown in FIGS. 6a and 6c-d, the leaves 404a, 404b, 404c and 404d form a square aperture 410. The leaves 404a, 404b, 404c, 404d have a trapezoidal shape with a straight edge that is oriented to form a square aperture 410. In other aspects, a leaf 404 can take various shapes and forms. However, it is preferred that the leaves 404a, 404b, 404c, 404d are shaped according to the size of the aperture 410 for which is desired. Other shapes and number of leafs can be used to form various shaped apertures. In addition, the number of gears 402, arms 403, and leaves 404 can be determined based upon the shape of the aperture that is desired. For example, if a triangular aperture 410 is desired, three leaves 404, three gears 402 and three arms 403 can be used.

In an aspect, rotational movement of gears 402a, 402b, 402c and 402d is accomplished by attaching a driving mechanism 420. In an aspect, the driving mechanism 420 comprises a drive motor 420 to a dowel pin (not shown) associated with each gear 402. FIG. 6c illustrates an embodiment of the present invention where a drive motor 420 is attached to the dowel pin of gear 402c. In an aspect, the drive motor 420 is a stepper motor; however, the drive motor 420 could be a DC motor, AC motor, or any other suitable motor. In addition, any motor controller with positional feedback can control the motor. In an aspect, the motor controller would be linked with the robotic arm 303, the control system 304, and/or the computer 305 implementing the treatment plan system.

As previously mentioned, rotational movement of the gears 402 is used to control the position of each leaf 404. In an aspect, the positions of the leaves 404 can be controlled with two separate drive motors 420—one motor for each orthogonal leaf direction. In another aspect, three drive motors 420 can be used to control the position of the leaves—one motor 420 to control a parallel leaf pair (e.g. 404a and 404c), and the other two drive motors 420 to control the remaining two leaves (e.g. 404b and 404d) independently. In another aspect, four drive motors 420 can be used to control each leaf 404 independently. In other embodiments of the present invention, one or more drive motors 420 can be used for added redundancy. As such, the drive motors 420 can be configured to take control of the leaves 402 that are associated with one or more motors 420 that incidentally fail during operation.

In an aspect, ach teeth/cog area 401, smaller gear 402, gear arm 403, leaf 404, leaf arm 405, including their pivoting connections, and driving mechanism 420 form a leaf assembly with their respective connected components (e.g., 401a, 402a, 403a, 404a, 405a, and 420). In such aspects, the combination of the teeth/cog area 401, smaller gear 402, gear arm 403 and leaf arm 405, including their pivoting connections, form a motion translation assembly that translates the motion of the driving mechanism 420 (e.g., a drive motor 420) to move the leaf 404 in a linear motion.

FIG. 7 illustrates a radiation dose measurement for a collimator according to an aspect of the present invention. The area 500 below the aperture 410 received 7 Gy radiation dose, while the area 501 below the leaves 404a, 404b, 404c and 404d received 0.2 Gy radiation dose, showing that the collimation system 301 and its components effectively blocks most radiation outside of the aperture 410.

As discussed above, current IORT devices can only deliver a uniform-intensity radiation dose to a surface. The systems 100, 200, 300 described above provides clinicians with the ability to deliver tumor-conformal IORT with unprecedented accuracy, reducing dose to neighboring healthy tissues and therefore minimizing the complication probability and improving quality of life for the patient.

Figure 8:
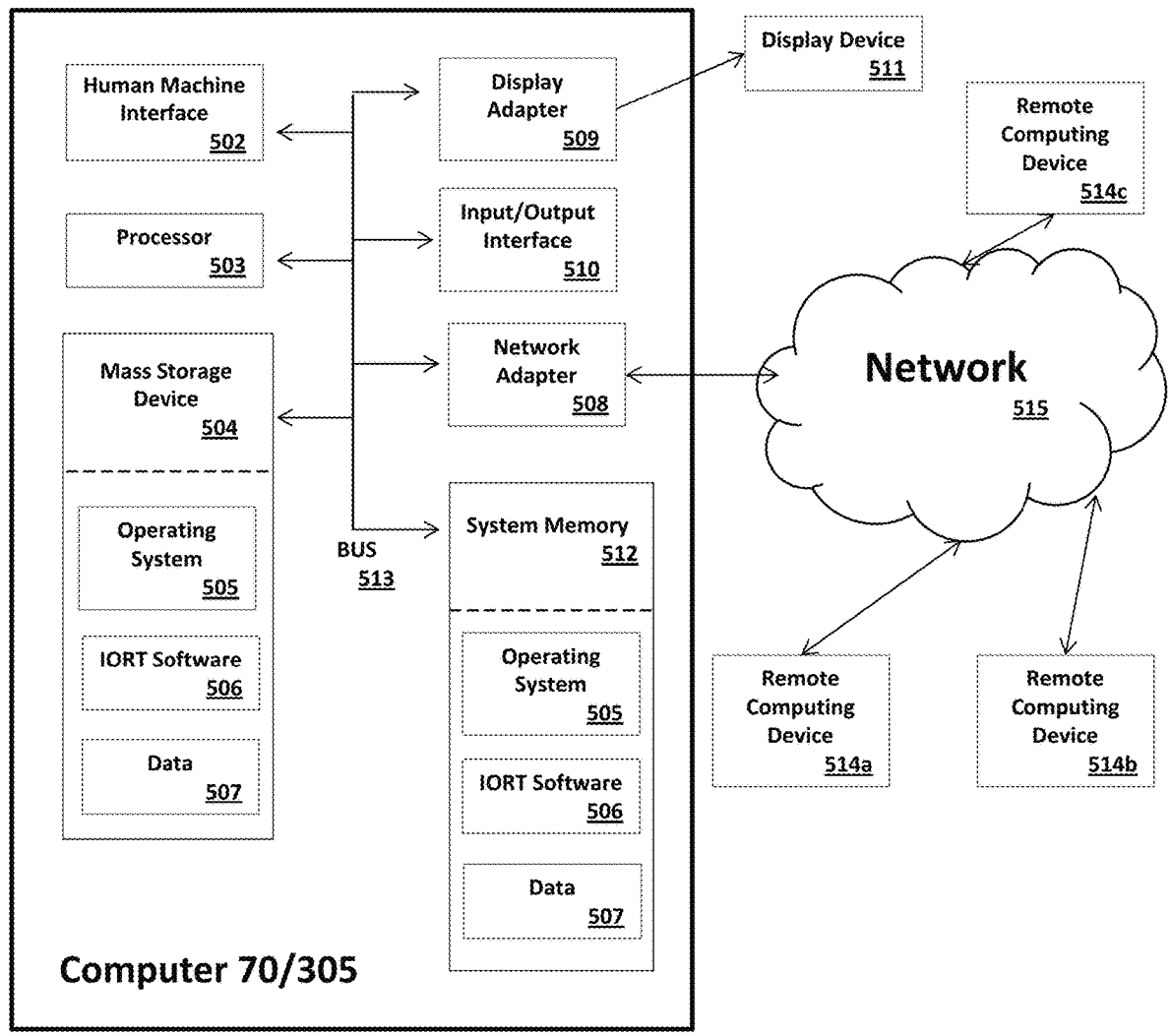
FIG. 8 is a block diagram of a computer according to an aspect of the present invention.

As discussed above, the LexRT systems 100, 200, 300 can be configured to be controlled by computerized means 70/305. The computerized means 70/305 can include a fast dose application, treatment plan, and signal processing software, discussed in more detail below. FIG. 8 is a block diagram illustrating an exemplary computer 70/305 for performing a portion of disclosed methods according to an embodiment of the present invention. This exemplary computer 70/305 is only an example of an operating environment and is not intended to suggest any limitation as to the scope of use or functionality of operating environment architecture. Neither should the computer 70/305 be interpreted as having any dependency or requirement relating to any one or combination of components illustrated in the exemplary operating environment.

Further, one skilled in the art will appreciate that the systems and methods disclosed herein can utilize a general-purpose computing device in the form of a computer 70/305. The methods discussed above can be performed by the computer 70/305. For example, the computer 70/305 can perform the duties and responsibilities of the controller discussed above.

The components of the computer 70/305 can comprise, but are not limited to, one or more processors or processing units 503, a system memory 512, and a system bus 513 that couples various system components including the processor 503 to the system memory 512. In the case of multiple processing units 503, the system can utilize parallel computing.

The system bus 513 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 513, and all buses specified in this description can also be implemented over a wired or wireless network connection and each of the subsystems, including the processor 503, a mass storage device 504, an operating system 505, IORT software 506, data 507, a network adapter 508, system memory 512, an Input/Output Interface 510, a display adapter 509, a display device 511, and a human machine interface 502, can be contained within one or more remote computing devices 514a,b,c at physically separate locations, connected through buses of this form, in effect implementing a fully distributed system.

The computer 70/305 typically comprises a variety of computer readable media. Exemplary readable media can be any available media that is accessible by the computer 70/305 and comprises, for example and not meant to be limiting, both volatile and non-volatile media, removable and non-removable media. The system memory 512 comprises computer readable media in the form of volatile memory, such as random access memory (RAM), and/or non-volatile memory, such as read only memory (ROM). The system memory 512 typically contains data such as data 507 and/or program modules, such as operating system 505 and IORT software 506, that are immediately accessible to and/or are presently operated on by the processing unit 503. In an aspect, the IORT software 506 can be configured to control the various systems of the LexRT system 100, including, but not limited to, the collimator systems 110, 210, 301 and the 3D real-time imaging system 60, and be configured to be able to process signals from the real-time 3D surface imaging system 60, and calculating an accurate radiation dose.

In another aspect, the computer 70/305 can also comprise other removable/non-removable, volatile/non-volatile computer storage media. By way of example, FIG. 8 illustrates a mass storage device 504, which can provide non-volatile storage of computer code, computer readable instructions, data structures, program modules, and other data for the computer 70/305. For example and not meant to be limiting, a mass storage device 504 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 504, including by way of example, an operating system 505 and the IORT software 506. Each of the operating system 505 and IORT software 506 (or some combination thereof) can comprise elements of the programming and the IORT software 506. Data 507 can also be stored on the mass storage device 504. Data 507 can be stored in any of one or more databases known in the art. Examples of such databases include DB2®, Microsoft® Access, Microsoft® SQL Server, Oracle®, mySQL, PostgreSQL, and the like. The databases can be centralized or distributed across multiple systems.

In another aspect, the user can enter commands and information into the computer 70/305 via an input device (not shown). Examples of such input devices comprise, but are not limited to, a keyboard, pointing device (e.g., a "mouse"), a microphone, a joystick, a scanner, tactile input devices such as gloves, cameras, and other body coverings, and the like. These and other input devices can be connected to the processing unit 503 via a human machine interface 502 that is coupled to the system bus 513, but can be connected by other interface and bus structures, such as a parallel port, game port, an IEEE 1394 Port (also known as a Firewire port), a serial port, or a universal serial bus (USB).

In yet another aspect, a display device 511 can also be connected to the system bus 513 via an interface, such as a display adapter 509. It is contemplated that the computer 501 can have more than one display adapter 509 and the computer 501 can have more than one display device 511. For example, a display device can be a monitor, an LCD (Liquid Crystal Display), or a projector. In addition to the display device 511, other output peripheral devices can comprise components such as speakers (not shown) and a printer (not shown) which can be connected to the computer 501 via Input/Output Interface 510. Any step and/or result of the methods can be output in any form to an output device. Such output can be any form of visual representation, including, but not limited to, textual, graphical, animation, audio, tactile, and the like.

The computer 70/305 can operate in a networked environment using logical connections to one or more remote computing devices 514a,b,c. By way of example, a remote computing device can be a personal computer, a laptop computer, portable computer, a server, a router, a network computer, a peer device or other common network node, and so on. Logical connections between the computer 70/305 and a remote computing device 33a,b,c can be made via a local area network (LAN) and a general wide area network (WAN). Such network connections can be through a network adapter 508. A network adapter 508 can be implemented in both wired and wireless environments. Such networking environments are conventional and commonplace in offices, enterprise-wide computer networks, intranets, and the Internet 515.

According to an aspect, the computer 70/305, via the IORT software 506, can control the operation of the LexRT systems 100, 300 according to an aspect.

For purposes of illustration, application programs and other executable program components such as the operating system 505 are illustrated herein as discrete blocks, although it is recognized that such programs and components reside at various times in different storage components of the computing device 70/305, and are executed by the data processor(s) of the computer. An implementation of the IORT software 506 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An aperture shaping device configured for use with a low energy radiation beam, the aperture shaping device comprising:
    a. a plurality of leaf assemblies, the leaf assemblies comprising:
        i. a leaf configured to interact with the low energy radiation beam;
        ii. a driving mechanism configured to drive the leaf to interact with the low energy radiation beam; and
        iii. a motion translation assembly configured to translate a first motion from the driving mechanism to a second motion for the leaf to travel, the motion translation assembly comprises a connecting wire connected to the driving mechanism and the leaf, wherein the first motion comprises a linear motion from the driving mechanism and the second motion is a different linear direction of travel for the leaf, and wherein the leaves are oriented to form the aperture.

2. The aperture shaping device of claim 1, wherein the different linear direction of travel for the leaf is rotated approximately ninety degrees from the linear motion of the driving mechanism.

3. The aperture shaping device of claim 2, wherein the linear direction of the driving mechanism is vertical, allowing the driving mechanism to be oriented vertically above the leaf.

4. The aperture shaping device of claim 1, wherein the driving mechanism comprises:
    a stepper motor;
    a lead screw; and
    a nut connected to the connecting wire, wherein the stepper motor rotationally drives the lead screw to drive the nut to drive the connecting wire in a linear direction.

5. The aperture shaping device of claim 1, wherein at least one of the plurality of leaf assemblies further comprises a compression spring engaged with the leaf.

6. The aperture shaping device of claim 1, wherein the driving mechanism and the motion translation assembly of at least one of the plurality of leaf assemblies are pivotably connected to one another.

7. The aperture shaping device of claim 1, wherein each of the plurality of leaf assemblies is configured to operate independently of each other.

8. The aperture shaping device of claim 1, wherein the driving mechanism is oriented above the leaf for at least one of the plurality of leaf assemblies.

9. The aperture shaping device of claim 1, wherein the motion translation assembly is further configured to translate a rotational motion from the driving mechanism to the first linear motion.

10. The aperture shaping device of claim 9, further comprising:
    b. an outer housing configured to attach to a radiation source supplying the low energy radiation beam; and
    c. an inner large gear configured to engage the outer housing and contain the plurality of leaf assemblies.

11. The aperture shaping device of claim 10, wherein the motion translation assembly comprises a smaller gear, wherein the smaller gear is connected to and driven by the driving mechanism and pivotably connected to the leaf at a first end of the leaf, and wherein the leaf is pivotably connected to the housing at a second end.

12. A low energy radiation x-ray radiation therapy system for use at a target within a cavity of a subject, the system comprising:
    a. a low energy radiation source configured to generate a radiation beam;
    b. a computer configured to communicate with the surface monitoring system; and
    c. an aperture shaping device configured to shape the radiation beam, the aperture shaping device comprising:
        i. a housing;
        ii. a plurality of leaf assemblies mounted on the housing, each of the leaf assemblies comprising:
            A. a leaf configured to interact with the low energy radiation beam;
            B. a driving mechanism configured to drive the leaf to interact with the low energy radiation beam; and C. a motion translation assembly comprising a connecting wire connecting the driving mechanism and the leaf, the motion translation assembly configured to translate a first linear motion from the driving mechanism to a second linear direction of travel for the leaf, the first linear motion different from the second linear direction, wherein the leaves are oriented to form the aperture.

13. The system of claim 12, wherein the plurality of leaf assemblies are configured to operate independently of one another.

14. The system of claim 12, wherein the computer is configured to control the plurality of leaf assemblies.

15. The system of claim 12, wherein for each of the plurality of leaf assemblies, the driving mechanism and the motion translation assembly are pivotably connected to one another.

16. The system of claim 15, wherein the driving mechanism comprises a linear actuator pivotably connected to a connecting rod, wherein the connecting wire of the motion translation assembly is pivotably connected to the connecting rod and the leaf.

17. The system of claim 16, further comprising a surface monitoring system configured to generate images of the target.

* * * * *